(12) United States Patent
Irioka et al.

(10) Patent No.: US 6,551,245 B1
(45) Date of Patent: Apr. 22, 2003

(54) ULTRASONIC PROBE

(75) Inventors: Kazuyoshi Irioka, Sagamihara (JP); Eiichi Ookawa, Yokohama (JP); Jun Koizumi, Yokohama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/708,643

(22) Filed: Nov. 9, 2000

(30) Foreign Application Priority Data

Nov. 26, 1999 (JP) .......................................... 11-336353

(51) Int. Cl.⁷ .................................................. A61B 8/00
(52) U.S. Cl. ...................... 600/444; 600/463; 600/437; 600/459
(58) Field of Search ................................ 600/459, 444, 600/463; 128/916

(56) References Cited

U.S. PATENT DOCUMENTS 4,895,158 A * 1/1990 Kawabuchi et al. ........ 600/463
5,152,294 A * 10/1992 Mochizuki et al. ......... 128/916
5,630,416 A * 5/1997 Uchikura et al. ........... 600/444

FOREIGN PATENT DOCUMENTS

JP  5-337108  12/1993

\* cited by examiner

Primary Examiner—Marvin M. Lateef
Assistant Examiner—Ruby Jain
(74) Attorney, Agent, or Firm—Connolly Bove Lodge & Hutz LLP

(57) ABSTRACT

An ultrasonic probe is provided which may be employed in medical applications to radiate an ultrasonic wave for inspecting the interior of a patient's body noninvasively. The ultrasonic probe includes a scan mechanism which consists of a rotating mechanism and a swinging mechanism. The rotating mechanism is designed to rotate a cylindrical holder having installed thereon a piezoelectric element which emits an ultrasonic wave and receives the echo. The swinging mechanism is designed to swing a rotary base which supports the rotating mechanism to swing the cylindrical holder about an axis of rotation extending perpendicular to that of the piezoelectric element.

9 Claims, 9 Drawing Sheets

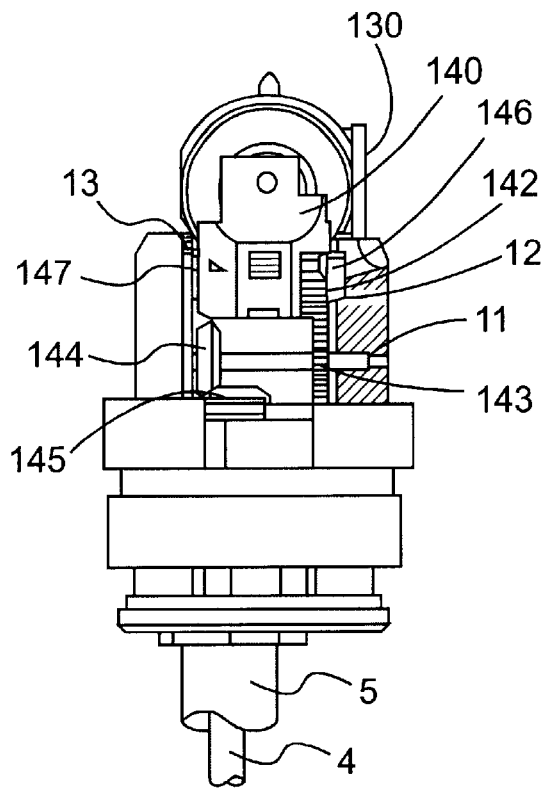
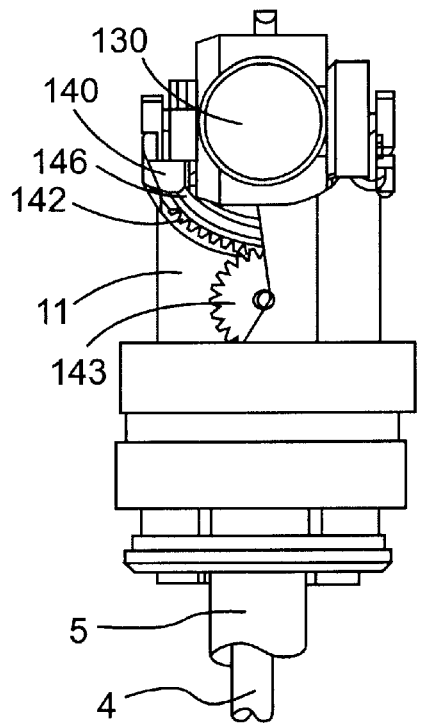
FIG. 3A   FIG. 3B
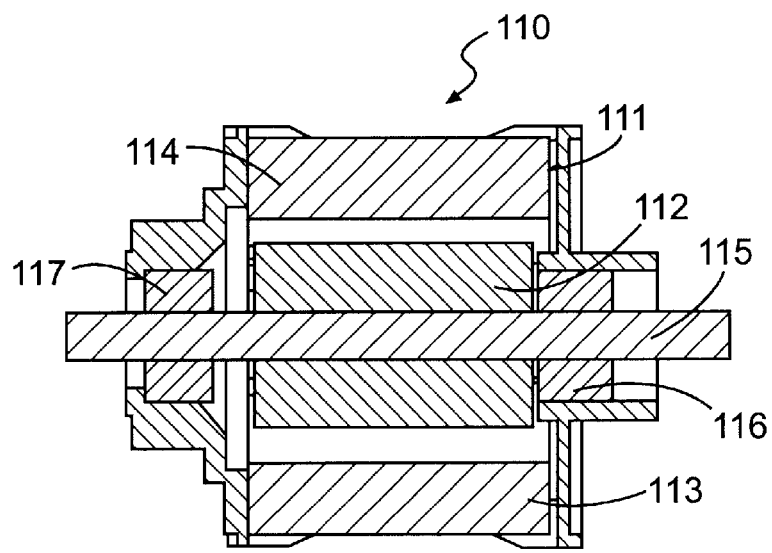
FIG. 4

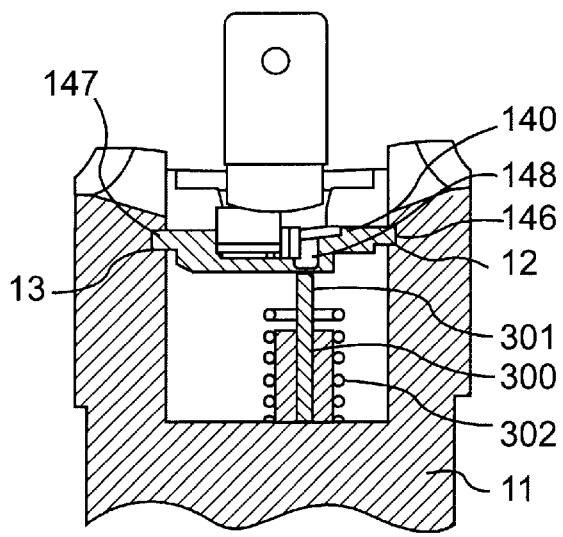
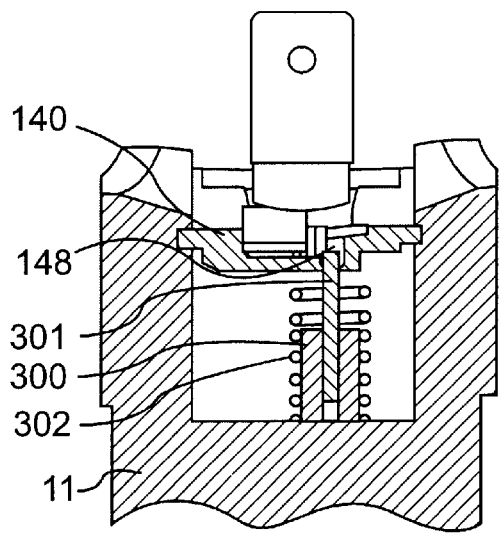
FIG. 8A  FIG. 8B
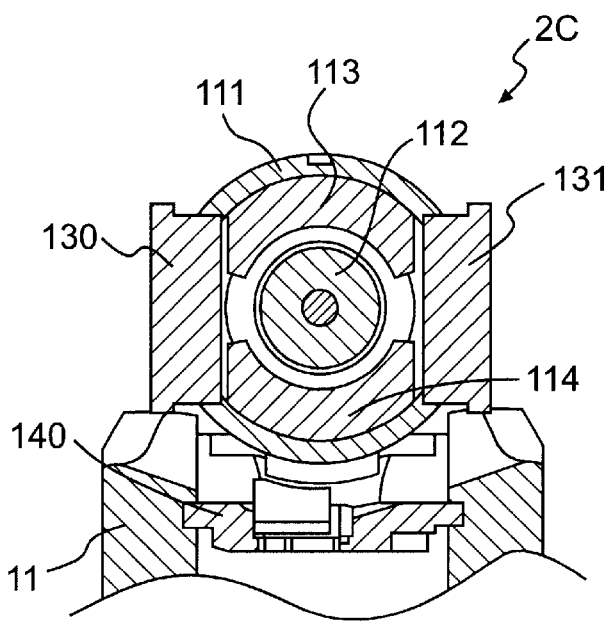
FIG. 9

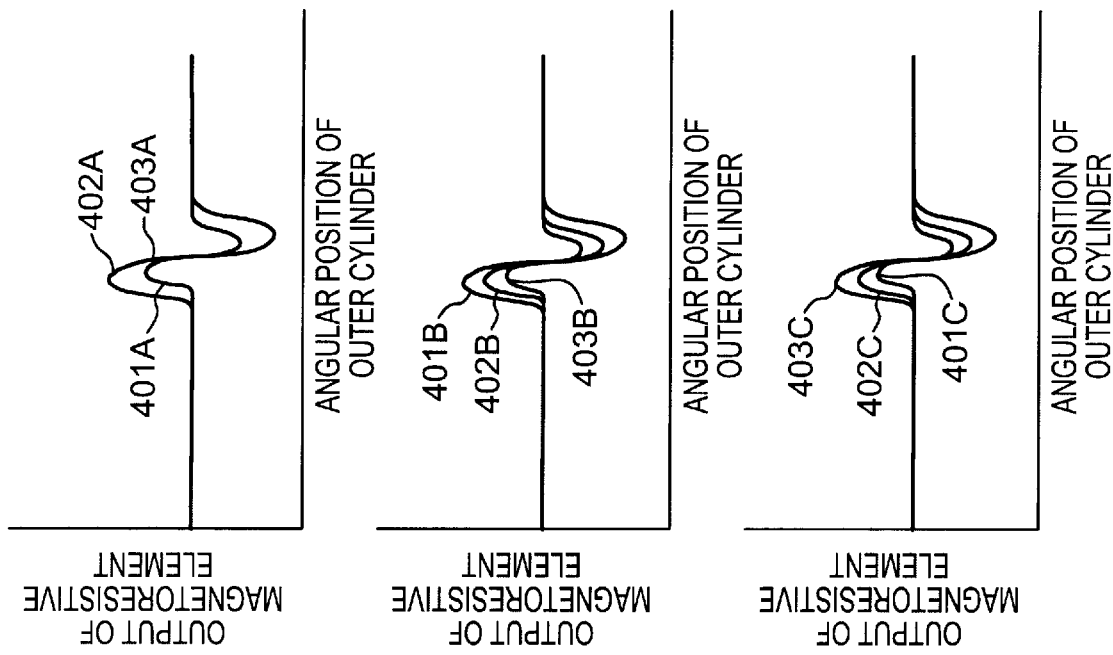
FIG. 15a
FIG. 15b
FIG. 15c
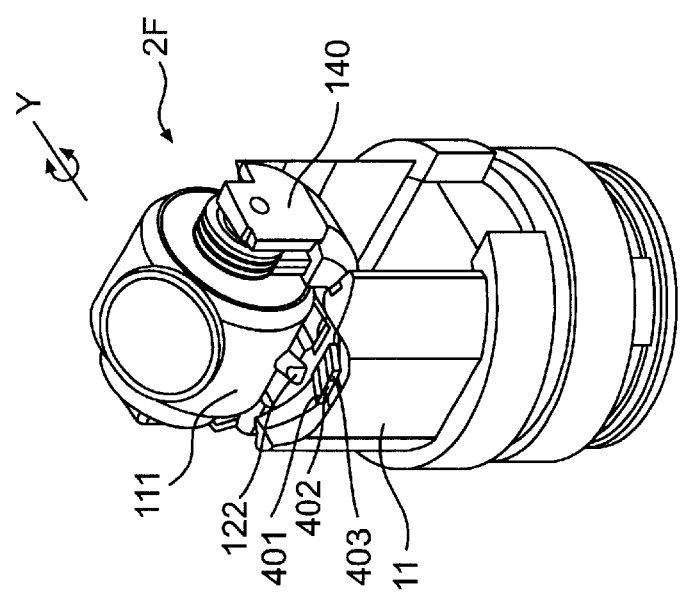
FIG. 14

ULTRASONIC PROBE

BACKGROUND OF THE INVENTION

1. Technical Field of the Invention

The present invention relates generally to an ultrasonic probe which is used in, for example, medical applications to radiate an ultrasonic wave for inspecting the interior of a patient's body noninvasively, and more particularly to an improved structure of a scan mechanism of an ultrasonic probe designed to rotate a piezoelectric element emitting the ultrasonic wave.

2. Background Art

Japanese Patent First Publication No. 5-337108 teaches a scan mechanism for an ultrasonic probe. The scan mechanism includes a rotor having a piezoelectric element installed thereon and two electric motors one of which rotates the piezoelectric element about a first axis and other of which swings the piezoelectric element about a second axis perpendicular to the first axis.

The scan mechanism is, however, complex and bulky in structure and encounters the drawback in that it is difficult to use the ultrasonic probe in a small cavity of a person's body, for example.

SUMMARY OF THE INVENTION

It is therefore a principal object of the present invention to avoid the disadvantages of the prior art.

It is another object of the present invention to provide a simple, lightweight, and inexpensive structure of a scan mechanism of an ultrasonic probe designed to rotate a piezoelectric element emitting an ultrasonic wave.

According to one aspect of the invention, there is provided an ultrasonic probe which comprises: (a) a piezoelectric element emitting an ultrasonic wave and receiving an echo thereof, the piezoelectric element converting the echo into an electric signal; (b) a holding member holding the piezoelectric element; (c) a rotating mechanism rotating the holding member about a first axis; (d) a rotary base supporting the rotating mechanism; (e) a chassis supporting the rotary base so as to allow the rotary base to swing about a second axis extending in a direction different from the first axis; and (f) a swinging mechanism swinging the rotary base.

In the preferred mode of the invention, the rotating mechanism includes a holding member angular position measuring encoder designed to measure an angular position of the holding member.

The holding member angular position measuring encoder may include a first encoder unit and a second encoder unit each of which is made of a magnetic member and a magnetoresistive element. The first encoder unit is designed to measure a change in angular position of the holding member by rotation about the first axis. The second encoder unit is designed to measure a preselected reference angular position of the holding member.

The rotating mechanism includes a holding member rotating electric motor rotating the holding member made of a rotary cylinder, a conductive cylinder arranged in alignment of a central axis with a central axis of the rotary cylinder, and a conductive brush installed on the rotary base in contact with the conductive cylinder.

The rotating mechanism may alternatively include a holding member rotating electric motor rotating the holding member made of a rotary cylinder, a first coil installed on the rotary cylinder, and a second coil installed on the rotary base so as to face the first coil. The first coil is responsive to a change in magnetic flux of the second coil to produce an electric signal for energizing the piezoelectric element.

The swinging mechanism includes a rotary base swinging electric motor, an motor angular position measuring encoder measuring an angular position of the rotary base swinging electric motor, and a gear train transmitting output torque of the rotary base swinging electric motor to the rotary base to swing the rotary base.

The swinging mechanism may alternatively include a voice coil motor and a rotary base angular position measuring encoder which measures an angular position of the rotary base. The voice coil motor is implemented by a magnet installed on one of the rotary base and the chassis and an electric coil installed on the other of the rotary base and the chassis.

A holding mechanism may also be provided which is designed to hold the rotary base on the chassis.

A second piezoelectric element may further be installed on the holding member which produces an ultrasonic wave having the same frequency of that produced by the piezoelectric element.

The second piezoelectric element may alternatively be designed to produce an ultrasonic wave having a frequency different from that produced by the piezoelectric element.

A magnetoresistive element may also be provided which is responsive to a change in magnetic flux produced by the magnetic member of the second encoder to provide a signal indicative of a neutral position of the holding member in swinging motion of the holding member.

An array of magnetoresistive elements may also be installed on the chassis. Each of the magnetoresistive elements is responsive to a change in magnetic flux produced by the magnetic member of the second encoder to provide a signal indicative thereof.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 3(a) is a side view which shows a side of the rotor motor of FIG. 2;

FIG. 3(b) is a side view which shows a side of the rotor motor opposed to FIG. 3(a);

FIG. 4 is a sectional view which shows an internal structure of the rotor motor of FIG. 2;

FIG. 8(a) is a partially sectional view which shows a lock mechanism used in the rotor motor of FIG. 7;

FIG. 8(b) is a partially sectional view which shows a side of the lock mechanism opposed to FIG. 8(a);

FIG. 9 is a partially sectional view which shows a rotor motor according to the fourth embodiment of the invention;

FIG. 14 is a perspective view which shows a rotor motor according to the seventh embodiment of the invention; and FIGS. 15(a) and, 15(b) and 15(c) show waveforms of signals outputted from an encoder in the seventh embodiment of the invention.

DESCRIPTION OF THE PREFERRED EMBODIMENTS

Figure 1:
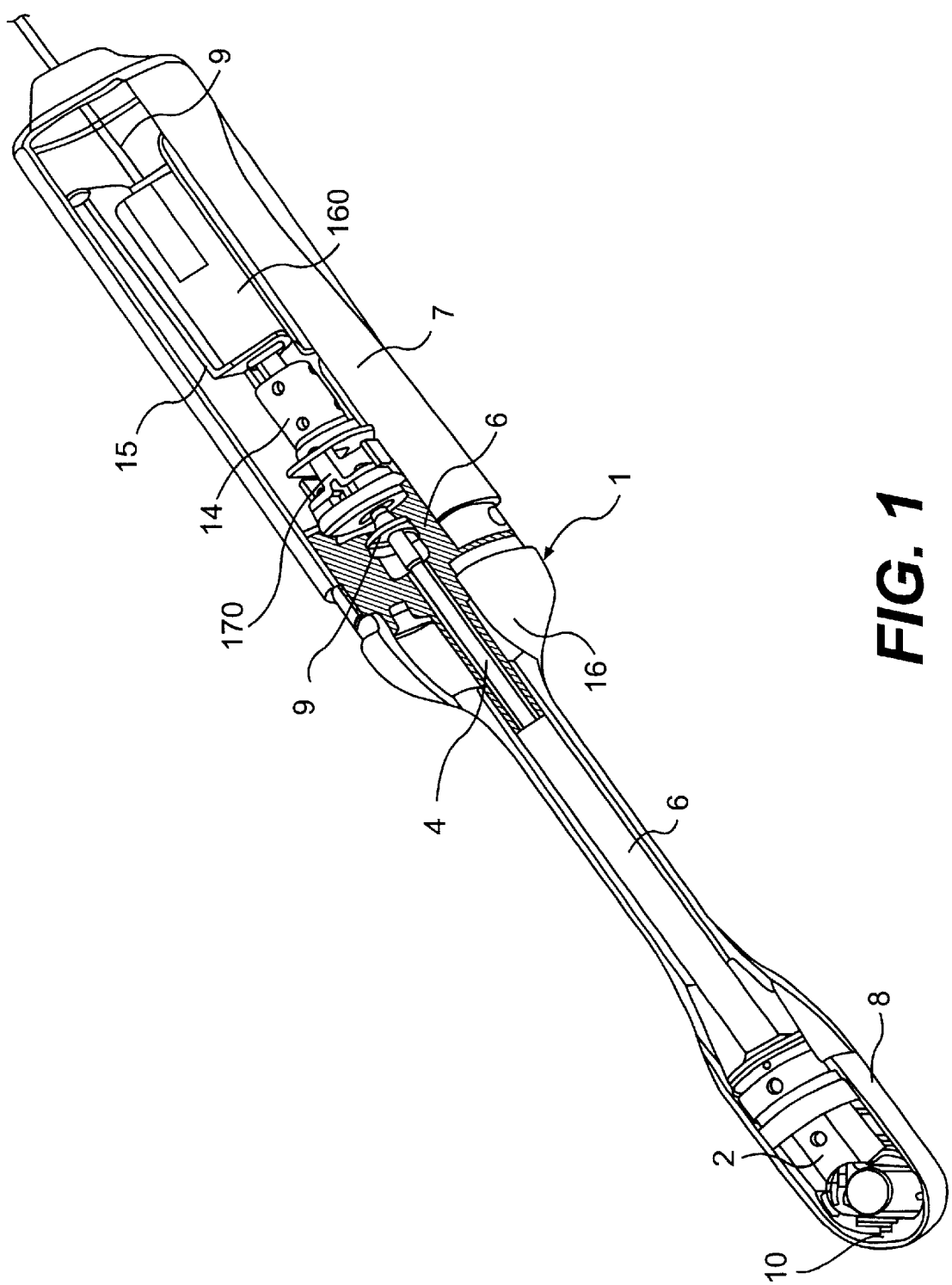
FIG. 1 a cutaway perspective view which shows an ultrasonic probe according to the first embodiment of the invention.

Referring now to the drawings, wherein like numbers refer to like parts in several views, particularly to FIG. 1, there is shown an ultrasonic probe 1 according to the first embodiment of the invention which may be employed in an ultrasonic diagnostic system designed to view the interior of a patient noninvasively.

The ultrasonic probe 1 includes a rotor motor 2, an electric signal transmitting wire 3, a drive shaft 4, a second encoder 170 (a first encoder will be described later), a second electric motor 160 (a first electric motor will be described later), a motor bracket 15, flexible joint 14, a pipe 5, a joint frame 6, a housing 7, a shaft holder 16, a window 8, and an oil seal 9.

The rotor motor 2 works to scan an ultrasonic wave. The second electric motor 160 rotates the drive shaft 4. The second encoder 170 measures a rotational angle of the drive shaft 4. The motor bracket 15 supports the second electric motor 160. The flexible joint 14 transmits the torque output of an output shaft of the second electric motor 160 to the drive shaft 4. The pipe 5 retains the rotor motor 2 and covers the drive shaft 4. The joint frame 6 supports the pipe 5. The housing 7 is fixed on the joint frame 6. The shaft holder 16 is fixed on the joint frame 6. The window 8 covers the rotor motor 2 and outputs the ultrasonic wave therethrough.

The inside of the window 8 is filled with a coupling liquid 10 in which the degree of attenuation of the ultrasonic wave is low. The oil seal avoids leakage of the coupling liquid 10 from a clearance between the drive shaft 4 and the pipe 5. For the brevity of illustration, the window 8, the shaft holder 16, the housing 7, the joint frame 6, and the pipe 5 are partially cut away in FIG. 1.

Figure 2:
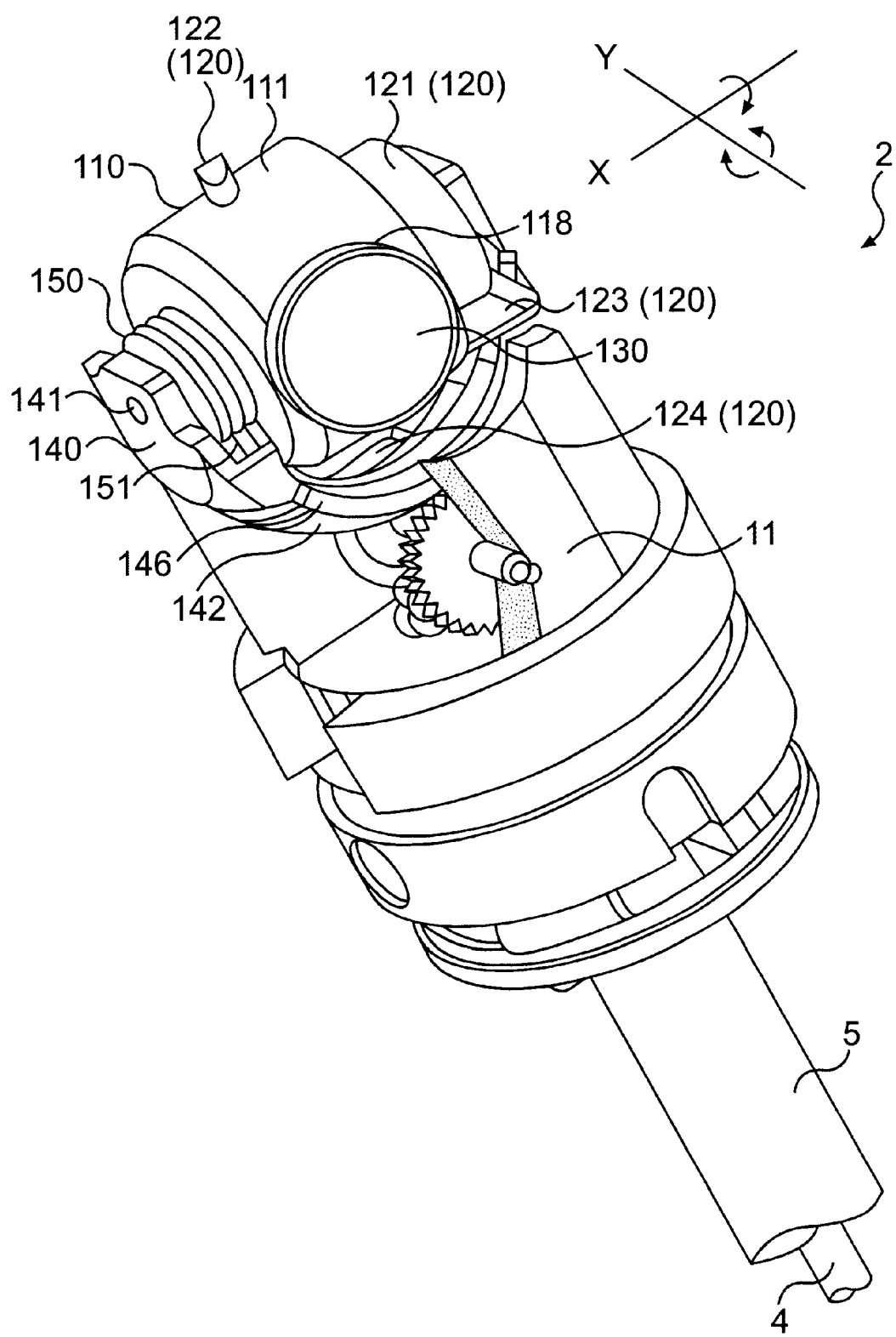
FIG. 2 is a perspective view which shows a rotor motor installed in the ultrasonic probe of FIG. 1.

FIG. 2 shows the structure of the rotor motor 2. For the convenience of illustration, a chassis 11 is partially cut away.

The rotor motor 2 includes the first electric motor 110. The first electric motor 110 has an outer cylinder 111 on which magnetic members 121 and 122 are installed. The magnetic member 121 is, as will be described later in detail, magnetized to have a given magnetic pattern for measuring an angular change of the outer cylinder 111. The magnetic member 122 is magnetized for determining a reference angular position of the outer cylinder 111. The outer cylinder 111 has formed thereon a mount 118 for mounting a piezoelectric element 130 and installed thereon a conductive cylinder 150 in alignment of the center thereof with an axis of rotation of the outer cylinder 111. The rotor motor 2 also includes a rotary base 140 which has formed therein a hole 141 for holding a central axis of the first electric motor 110 and installed thereon a magnetoresistive element 123 (i.e., a magnetroresistor) sensitive to a change in magnetic flux of the magnetic member 121 of the first encoder 120, a magnetoresistive element 124 sensitive to a change in magnetic flux of the magnetic member 122 of the first encoder 120, a conductive brush 151, and a first spur gear 142. On the chassis 11, a second spur gear 143 and a first bevel gear 144, as shown in FIGS. 3(a) and 3(b) are installed rotatably. The second spur gear 143 meshes with the first spur gear 142. The first bevel gear 144 is arranged coaxially with the second spur gear 143 and meshes with a second bevel gear 145 coupled to the drive shaft 4. The rotary base 140 has formed thereon arc-shaped protrusions or rails 146 and 147 which have a trapezoidal section and slidably engage grooves 12 and 13 formed in the chassis 11 to support the rotary base 140 so that it may swing.

Internally, the first electric motor 110, as shown in a sectional view of FIG. 4, includes an electric coil 112, permanent magnets 113 and 1 14, a central shaft 115, and bearings 116 and 117. The electric coil 112 is attached to the central shaft 115. The bearings 116 and 117 supports the outer cylinder 111 rotatably on the central shaft 115. The permanent magnets 113 and 114 are installed in the outer cylinder 111.

Figure 5:
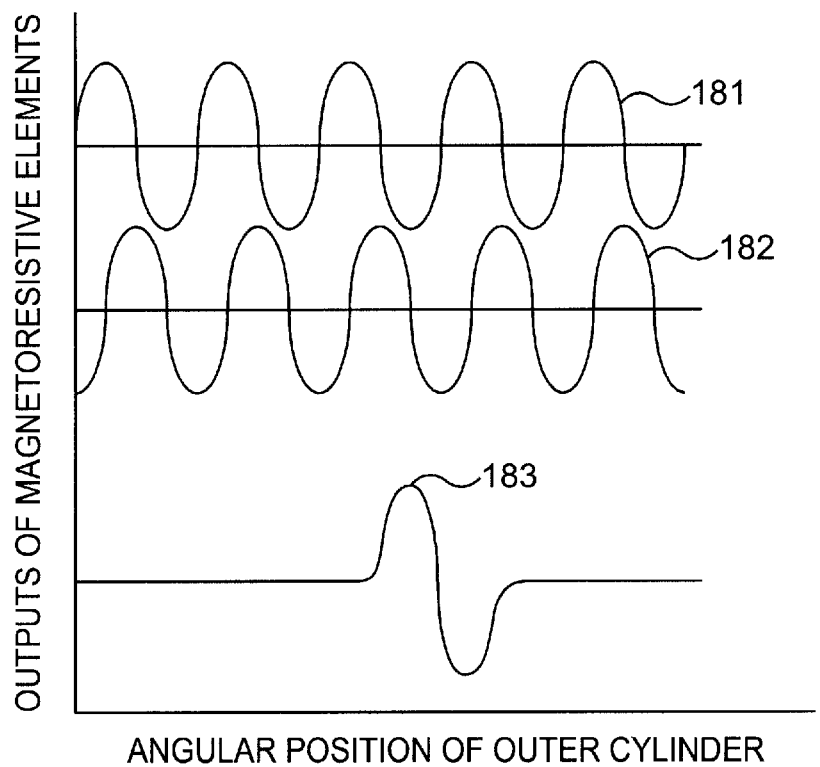
FIG. 5 is an illustration which shows output signals from an encoder measuring an angular position of a piezoelectric element.

FIG. 5 shows the waveform of signals outputted by the first encoder 120. The first encoder 120, as described above, consists of a first encoder unit designed to measure an angular change of the outer cylinder 111 caused by rotation of the outer cylinder 111 and a second encoder unit designed to detecting the reference angular position of the outer cylinder 111. The first encoder unit is made of the magnetic member 121 and the magnetoresistive element 123 which is sensitive to the magnetic pattern provided on the magnetic member 121 to produce electric signals, as discussed below. Similarly, the second encoder unit is made of the magnetic member 122 and the magnetoresistive element 124 which is magnetically responsive to the magnetic member 122 to produce an electric signal as discussed below. Specifically, the first encoder 120, as clearly shown in the drawing, outputs three signals: angular signals 181 and 182 and a reference angular signal 183. When the outer cylinder 111 is rotated about the central shaft 115, it will cause the angular signals 181 and 182 to change in level cyclically as shown in the drawing. A phase difference between the angular signals 181 and 182 indicates the direction of rotation of the outer cylinder 111. The number of pulses of each of the angular signals 181 and 182 represents a change in angular position of the outer cylinder 111. The reference angular signal 183 is produced whenever the second encoder unit reaches a preselected reference angular position, that is, whenever the magnetic member 122 passes the magnetoresistive element 124. The first encoder 120 resets the measured angular change of the outer cylinder 111 whenever the reference angular signal 183 is detected. In FIG. 5, the signals 181, 182, and 183 are illustrated as having different signal levels for convenience, however, these signal levels are, in fact, identical with each other.

In operation, an electric signal produced by an ultrasonic diagnostic system (not shown) is inputted in the form of a pulse signal to the conductive brush 151 installed on the rotary base 140 of the rotor motor 2 through the wire 3. The conductive brush 151 is in contact with the conductive cylinder 150 installed on the outer cylinder 111, so that the electric signal inputted to the conductive brush 151 is transmitted to the conductive cylinder 150. The conductive cylinder 150, although not shown in the drawings, is electrically connected to the piezoelectric element 130, so that the electric signal inputted to the conductive cylinder 150 is further transmitted to the piezoelectric element 130. The piezoelectric element 130 converts the inputted electric signal into oscillations to produce an ultrasonic wave and radiates it to the outside. If there is a reflective object in a propagation path of the ultrasonic wave, the ultrasonic wave is returned to the piezoelectric element 130. The piezoelectric element 130 converts the echo of the ultrasonic wave into an electric signal and outputs it to the ultrasonic diagnostic system through the conductive brush 151, the conductive cylinder 150, and the wire 130. The ultrasonic diagnostic system converts the input signal into an image signal using known imaging techniques.

During the radiation, the ultrasonic wave is scanned over 360° to produce an ultrasonic tomogram (i.e., an ultrasonogram) of the object. The scanning is achieved by energizing the electric coil 112 of the first electric motor 110 to rotate the outer cylinder 111 about the central shaft 115 (i.e., the x-axis in FIG. 2), thereby rotating the piezoelectric element 130. The angular position of the outer cylinder 111 is measured by the first encoder 120 to provide an angular position signal to the ultrasonic diagnostic system as indicating the position of a scanned portion of the object on the ultrasonic tomogram.

When it is required to shift the radiation of the ultrasonic wave (i.e., the scanned area of the object) in a direction perpendicular to the rotation of the outer cylinder 111, the second electric motor 160 is actuated to provide torque to the second bevel gear 145 through the drive shaft 4. The torque is subsequently transmitted to the first bevel gear 144 and to the first spur bear 142 through the second spur gear 143. The first spur gear 142 is installed on the rotary base 140, so that the rotary base 140 swings about the x-axis extending, as shown in FIG. 2, perpendicular to the y-axis along guide paths defined by slidable engagement of the rails 146 and 147 with the grooves 12 and 13 formed in the chassis 11. The angular position of the drive shaft 4 is measured by the second encoder 170 to provide an angular position signal to the ultrasonic diagnostic system as indicating the angular position of the rotary base 140 on the guide path.

As apparent from the above discussion, the first embodiment of the invention provides a simple and small-sized structure of the rotor motor 2 to enable the ultrasonic probe 1 to be constructed which is capable of producing an ultrasonic monogram of an object and measures the angular position of the head of the probe 1 with high and confidence levels.

Figure 6:
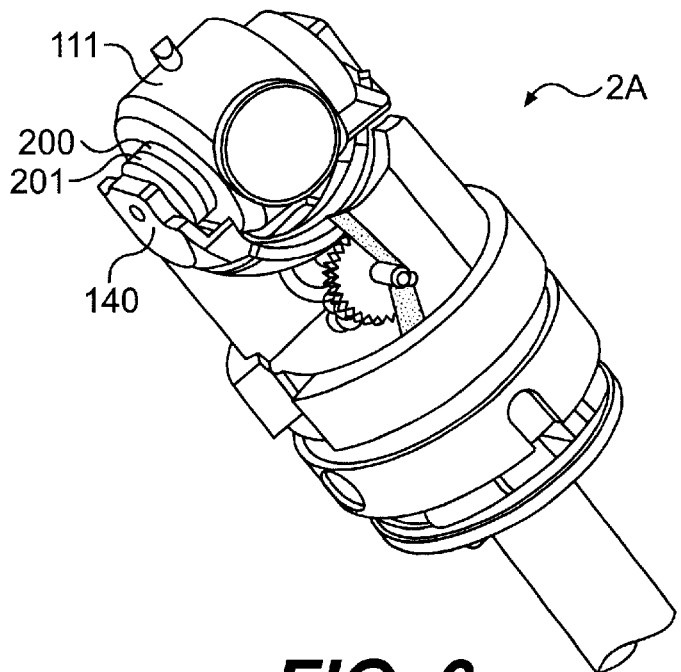
FIG. 6 is a perspective view which shows a rotor motor according to the second embodiment of the invention.

FIG. 6 shows a rotor motor 2A according to the second embodiment of the invention. The same reference numbers as employed in the first embodiment refer to the same parts, and explanation thereof in detail will be omitted here.

The rotor motor 2A is different from the rotor motor 2 of the first embodiment only in that the outer cylinder 111 has installed thereon the first coil 200 connected to the piezoelectric element 130, and the rotary base 140 has installed thereon the second coil 201 facing the first coil 200 with a given gap.

In operation, the ultrasonic diagnostic system provides a pulse signal of 80V to 200V to the second coil 201 through the wire 3. This causes the magnetic flux of the second coil 201 to be changed suddenly, thereby resulting in production of voltage at the first coil 200. The first coil 200 is, as described above, connected to the piezoelectric element 130, so that the voltage produced at the first coil 200 is applied to the piezoelectric element 130, thereby causing pulses to be radiated in the form of an ultrasonic wave. When the echo of the ultrasonic wave reaches the piezoelectric element 130, the piezoelectric element 130 converts the input into an electric signal in the form of a pulse signal outputs it to the first coil 200, so that the magnetic flux thereof is changed suddenly, thereby causing the second coil 201 to produce the voltage. The voltage is transmitted to the ultrasonic diagnostic system through the wire 3 and converted into an image signal.

The rotor motor 2A of this embodiment is, as apparent from the above, designed to establish signal transmission between a rotary member and a stationary member without mechanical sliding motion, thereby reducing the wear of parts of the ultrasonic probe.

Figure 7:
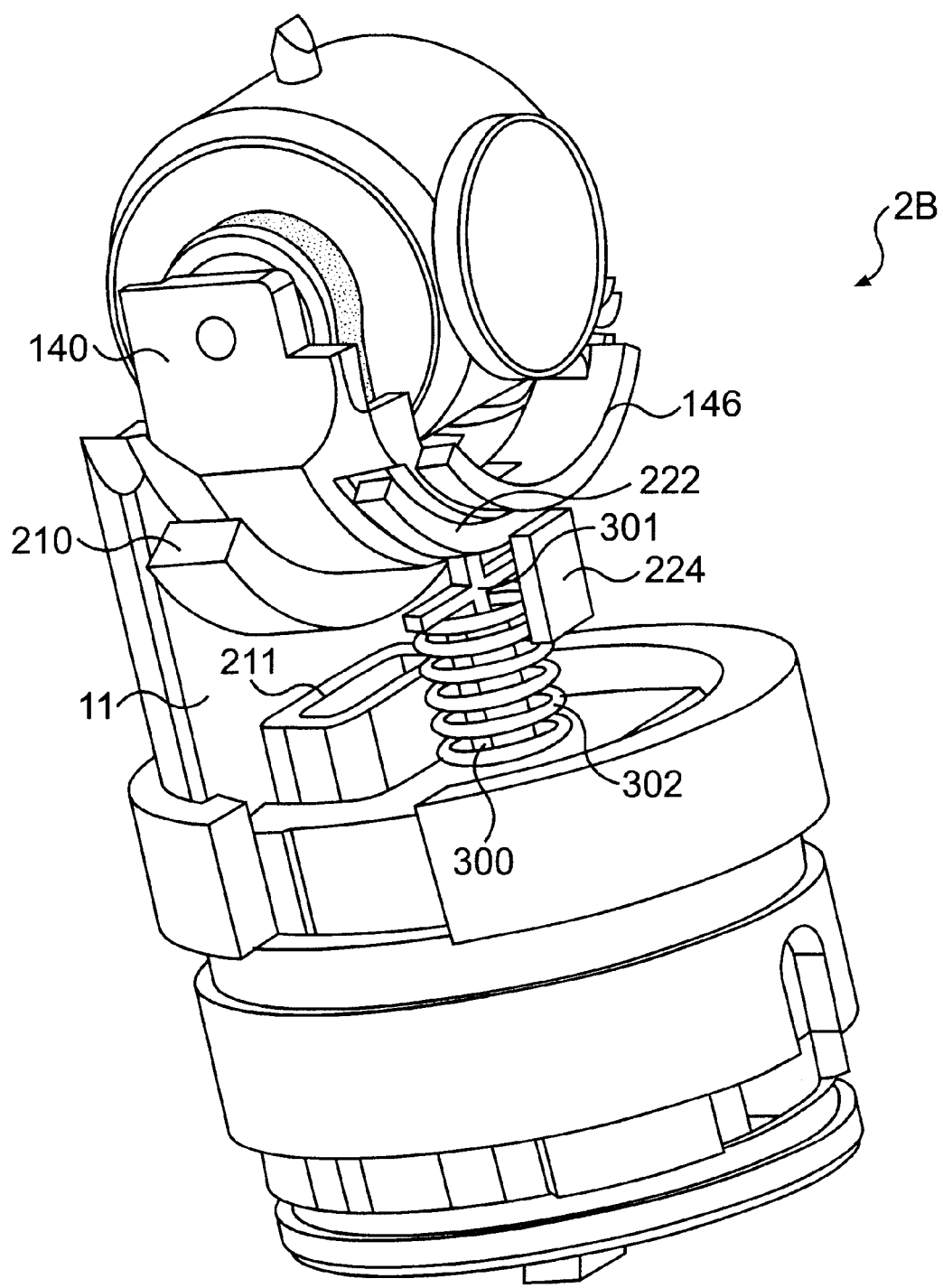
FIG. 7 is a perspective view which shows a rotor motor according to the third embodiment of the invention.

FIG. 7 shows a rotor motor 2B according to the third embodiment of the invention. The same reference numbers as employed in the first embodiment refer to the same parts, and explanation thereof in detail will be omitted here.

The rotary base 140, like the first embodiment, has formed thereon the arc-shaped rails 146 and 147 which engage, as shown in FIGS. 8(*a*) and 8(*b*), the grooves 12 and 13 formed in the chassis 11 slidably. The rotary base 140 has a magnet 210 installed thereon. The chassis 11 has installed thereon an electric coil 211 which forms a voice coil motor together with the magnet 210. The rotary base 140 has disposed thereon a magnetic member 222 magnetized to have a given magnetic pattern. The chassis 11 has disposed thereon a magnetoresistive element 224 which is sensitive to a change in magnetic field produced by the magnetic member 222. The rotary base 140 has also installed thereon a magnetic member (not shown) which is identical with the magnetic member 222. The chassis 11 has also installed thereon a magnetoresistive element (not shown) which is identical with the magnetoresistive element 224 and which measures a preselected neutral position of the rotary base 140 in the swing thereof in the same manner as that of the first encoder 120 in the first embodiment. These magnetic members and magnetoresistive elements form a swing angle measuring encoder. The rotary base 140 has, as shown in FIGS. 8(*a*) and 8(*b*), formed therein a hole 148 into which a lever 301 is inserted to hold he rotary base 140 in the chassis 11 fixedly. The lever 301 is urged by a coil spring 302 into constant engagement with the hole 148 and moved out of the engagement by a solenoid 300.

In operation, when the solenoid 300 is energized, it will cause the lever 301 to be attracted downward, as viewed in FIGS. 8(*a*) and 8(*b*), into disengagement from the hole 148, thereby allowing the rotary base 140 to rotate.

Subsequently, when the coil 211 disposed within a magnetic field produced by the magnet 210 is energized, it produces a magnetic force. The coil 211 is fixed on the chassis 11, so that a reactive force is produced which swings the rotary base 140 along the guide , paths defined by the rails 146 and 147 formed on the rotary base 140 and the grooves 12 and 13 formed in the chassis 11. The angular position of the rotary base 140 changed by the swing is measured by the swing angle measuring encoder. When it is required to hold the rotary base 140 from swinging, the solenoid 300 is reenergized to urge the lever 301 into engagement with the hole 148 in the rotary base 140 with aid of the spring load of the coil spring 302 to lock the rotary base 140.

The structure of the third embodiment is designed to swing the rotary base 140 without use of a gear train as employed in the second embodiment, thereby minimizing the wear of parts working to swing the rotary base 140. Further, when not in use, the lever 301 is fitted within the hole 148 formed in the rotary base 140 to lock the rotary base 140, thereby avoiding undesirable movement of the rotary base 140 during transportation of the ultrasonic probe, for example.

The electric coil 211 and the magnet 210 may alternatively be disposed on the chassis 11 and the rotary base 140, respectively.

FIG. 9 shows a rotor motor 2C according to the fourth embodiment of the invention which is different from the rotor motor 2 of the first embodiment only in that two piezoelectric elements 130 and 131 are installed on the outer cylinder 111 which produce oscillations at the same frequency. Other arrangements are identical, and explanation thereof in detail will be omitted here.

The rotor motor 2C may also use more than two piezoelectric elements for speeding up the acquisition of ultrasonograms.

Figure 10:
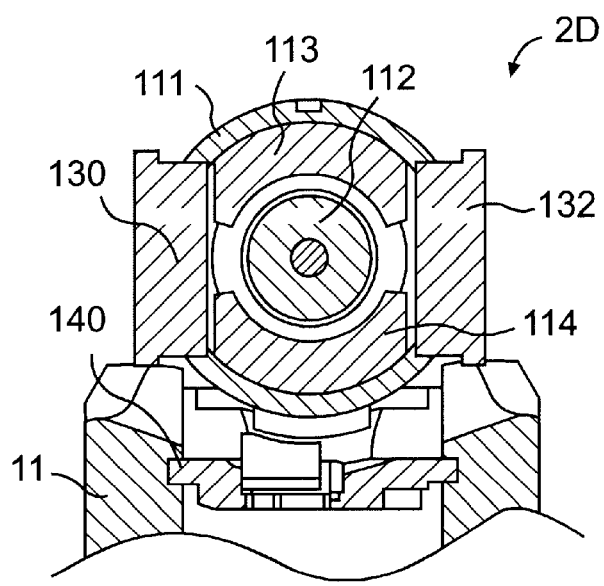
FIG. 10 is a partially sectional view which shows a rotor motor according to the fifth embodiment of the invention.

FIG. 10 shows a rotor motor 2D according to the fifth embodiment of the invention which is different from the rotor motor 2 of the first embodiment only in that two piezoelectric elements 130 and 132 are installed on the outer cylinder 111 which produce oscillations at different frequencies. Other arrangements are identical, and explanation thereof in detail will be omitted here.

Figure 11:
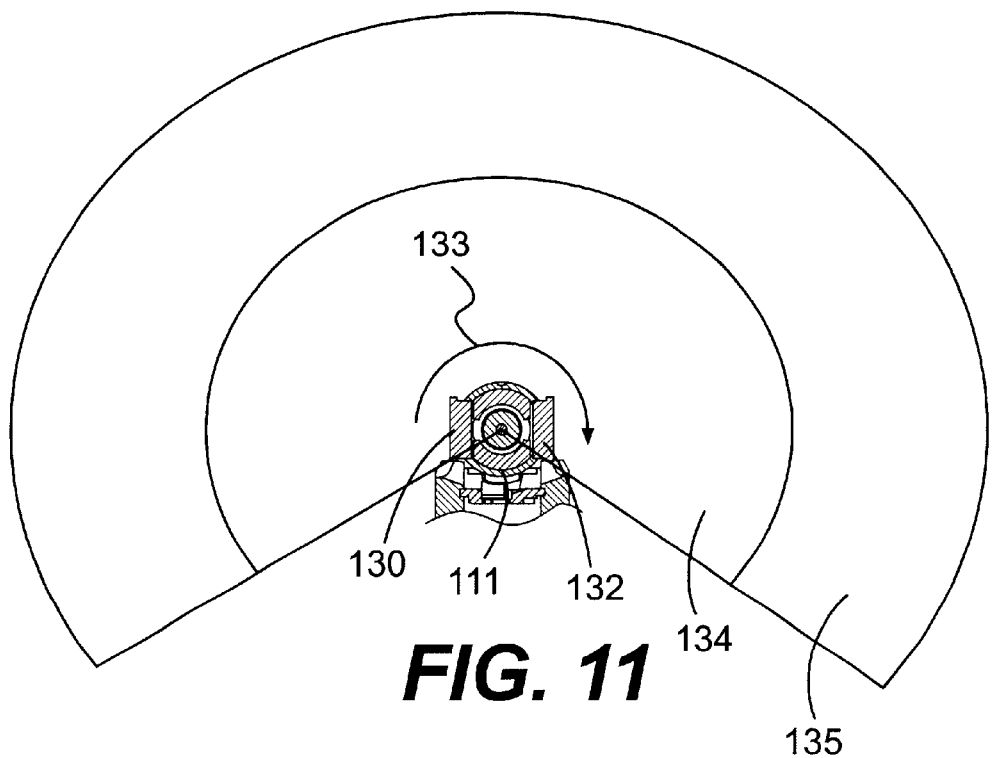
FIG. 11 is an illustration which shows a measurement range of an ultrasonic probe of the fifth embodiment of the invention.

When the ultrasonic wave passes through an object, as the frequency of the ultrasonic wave increases, the resolution becomes fine, but the degree of attenuation increases. Therefore, the use of ultrasonic wave having a higher frequency, enables acquisition of a finer ultrasonogram, but the distance to an object which allows an ultrasonogram to be formed decreases. Conversely, the use of ultrasonic wave having a lower frequency results in an increase in distance to an object which allows an ultrasonogram to be formed, but the resolution of the ultrasonogram decreases. The rotor motor 2D of this embodiment, as described above, uses the piezoelectric elements 130 and 132 producing oscillations having different frequencies and is designed to, as shown in FIG. 11, rotate the outer cylinder 111 in a direction as indicated by an arrow 133 to scan an angular area 134 using the higher frequency piezoelectric element 130 and an angular area 135 using the lower frequency piezoelectric element 132. Specifically, an ultrasonogram of a nearby portion of an object is derived by use of an ultrasonic wave having a higher frequency, thereby increasing the resolution of the ultrasonogram, while an ultrasonogram of a distance portion of the object is derived by use of an ultrasonic wave having a lower frequency, thereby increasing the distance the ultrasonic wave travels.

The rotor motor 2D may also use more than two piezoelectric elements producing oscillations having different frequencies.

Figure 12:
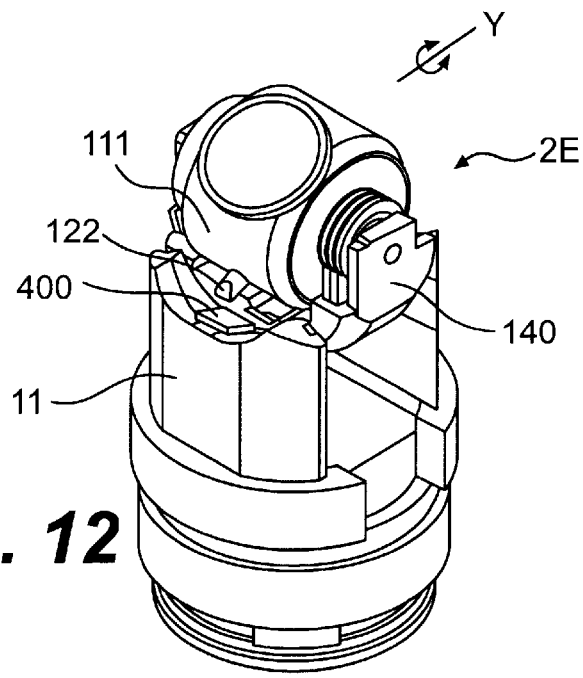
FIG. 12 is a perspective view which shows a rotor motor according to the sixth embodiment of the invention.

FIG. 12 shows a rotor motor 2E according to the sixth embodiment of the invention which is different from the rotor motor 2 of the first embodiment only in that a magnetroresistive element 400 is installed on the chassis 111 which is magnetically responsive to the magnetic member 122 to detect a neutral position of the outer cylinder 111 in swing of the rotary base 140 about the y-axis. Other arrangements are identical, and explanation thereof in detail will be omitted here.

Figure 13A:
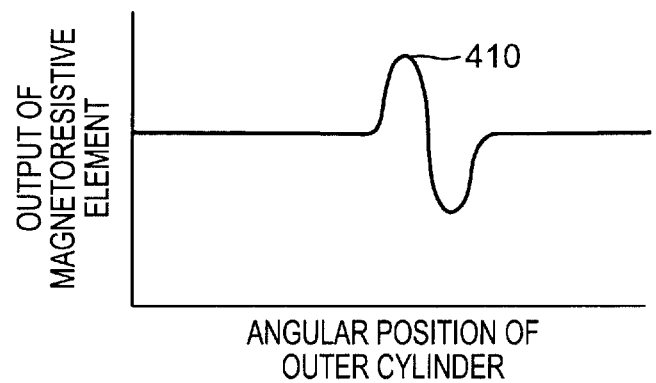
FIGS. 13(a) and 13(b) show waveforms of signals outputted from an encoder in the sixth embodiment of the invention.
Figure 13B:
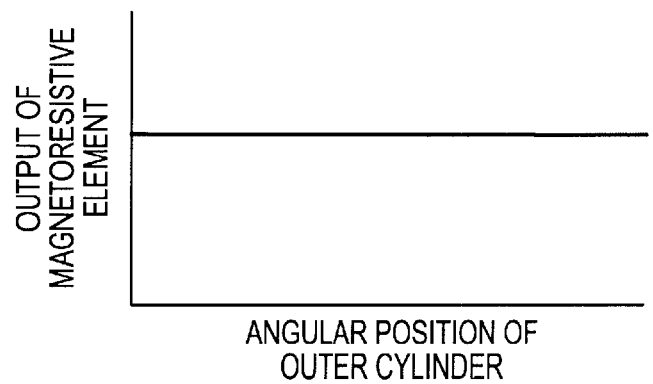

FIG. 13(*a*) shows the waveform of an output signal of the magnetoresistive element 400 during a 360° rotation of the outer cylinder 111 when the rotary base 140 is located at a swing angle of zero (i.e., the neutral position). FIG. 13(*b*) shows the waveform of an output signal of the magnetoresistive element 400 during a 360° rotation of the outer cylinder 111 when the rotary base 140 is swung along the guide paths, as described in the first embodiment. When the swing angle of the rotary base 140 is zero (0°), that is, when the rotary base 140 is in the neutral position, a complete rotation of the outer cylinder 111 causes the magnetic member 122 to pass the magnetoresistive element 400 disposed on the chassis 11 one time, thereby resulting in, as shown in FIG. 13(*a*), a peak output 410 of the magnetoresistive element 400. As the magnetic member 122 approaches the magnetoresistive element 400, the value of the peak 410 becomes great. When the rotary base 140 is swung from the neutral position, the magnetic member 122 moves away from the magnetoresisitve element 400, so that no peak is, as shown in FIG. 13(*b*), produced. The measurement of the neutral position of the rotary base 140 is, thus, achieved by swinging the rotary base 140 and monitoring the value of the peak of an output of the magnetoresistive element 400.

FIG. 14 shows a rotor motor 2F according to the seventh embodiment of the invention which is a modification of the sixth embodiment in which three magnetoresistive elements 401, 402, and 403 are so installed on the chassis 11 as to face the magnetic member 122 of the first encoder 120 used to detect the reference angular position of the outer cylinder 111. Other arrangements are identical with those in the sixth embodiment, and explanation thereof in detail will be omitted here.

FIG. 15(*a*) shows waveforms of output signals of the magnetoresistive elements 401, 402, and 403 during a 360° rotation of the outer cylinder 111 when the rotary base 140 is located at a swing angle of zero (i.e., the neutral position). 401A indicates the output of the magnetoresistive element 401. 402A indicates the output of the magentoresistive element 402. 403A indicates the output of the magnetoresistive element 403. FIG. 15(*b*) shows waveforms of output signals of the magnetoresistive elements 401, 402, and 403 during a 360° rotation of the outer cylinder 111 when the rotary base 140 is swung toward the magnetoresistive element 401 from the neutral position. 401B indicates the output of the magnetoresistive element 401. 402B indicates the output of the magentoresistive element 402. 403B indicates the output of the magnetoresistive element 403. FIG. 15(*c*) shows waveforms of output signals of the magnetoresistive elements 401, 402, and 403 during a 360° rotation of the outer cylinder 111 when the rotary base 140 is swung toward the magnetoresistive element 403 from the neutral position. 401C indicates the output of the magnetoresistive element 401. 402C indicates the output of the magentoresistive element 402. 403C indicates the output of the magnetoresistive element 403.

In operation, the direction of rotation of the outer cylinder 111 is determined by monitoring the levels of peaks of the outputs from the magnetoresistive elements 401, 402, and 403. Specifically, when the level of the peak of the output from the magnetoresistive element 401 is, as indicated by 401B in FIG. 15(*b*), greater than those of the magentoresistive elements 402 and 403, it is determined that the rotary base 140 being swinging close to the magnetoresistive element 401 from the neutral position. Alternatively, when the level of the peak of the output from the magnetoresistive element 403 is, as indicated by 403C in FIG. 15(*c*), greater than those of the magentoresistive elements 401 and 402, it is determined that the rotary base 140 being swinging close to the magnetoresistive element 403 from the neutral position. When the level of the peak of the output from the magnetoresistive element 402 is, as indicated by 401A in FIG. 15(a), the greatest of the three, and the levels of the outputs of the magnetoresistive elements 401 and 403 are equal to each other, it is determined that the rotary base 140 is in the neutral position.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. An ultrasonic probe comprising:

a piezoelectric element emitting an ultrasonic wave and receiving an echo thereof, said piezoelectric element converting the echo into an electric signal;

a holding member holding said piezoelectric element;

a rotating mechanism rotating said holding member about a first axis; said rotating mechanism including a holding member angular position measuring encoder designed to measure an angular position of said holding member;

said holding member angular position measuring encoder including a first encoder unit and a second encoder unit each of which is made of a magnetic member and a magnetoresistive element, the first encoder unit being designed to measure a change in angular position of said holding member by rotation about the first axis, the second encoder unit being designed to measure a preselected reference angular position of said holding member;

a rotary base supporting said rotating mechanism;

a fixed chassis supporting said rotary base so as to allow said rotary base to swing about a second axis extending in a direction different from the first axis; and a swinging mechanism swinging said rotary base.

2. An ultrasonic probe comprising:

a piezoelectric element emitting an ultrasonic wave and receiving an echo thereof, said piezoelectric element converting the echo into an electric signal;

a holding member holding said piezoelectric element;

a rotating mechanism rotating said holding member about the first axis;

a rotary base supporting said rotating mechanism;

a fixed chassis supporting said rotary base so as to allow said rotary base to swing about a second axis extending in a direction different from the first axis; and a swinging mechanism swinging said rotary base;

said rotating, mechanism including a -holding member rotating electric motor rotating said holding member made of a rotary cylinder, a conductive cylinder arranged in alignment of a central axis with a central axis of the rotary cylinder, and a conductive brush installed on said rotary base in contact with the conductive cylinder.

3. An ultrasonic probe comprising:

a piezoelectric element emitting an ultrasonic wave and receiving an echo thereof, said piezoelectric element converting the echo into an electric signal;

a holding member holding said piezoelectric element;

a rotating mechanism rotating said holding member about the first axis;

a rotary base supporting said rotating mechanism;

a fixed chassis supporting said rotary base so as to allow said rotary base to swing about a second axis extending in a direction different from the first axis; and a swinging mechanism swinging said rotary base;

said rotating mechanism including a holding member rotating electric motor rotating said holding member made of a rotary cylinder, a first coil installed on the rotary cylinder, and a second coil installed on said rotary base so as to face the first coil, said first coil being responsive to a change in magnetic flux of said second coil to produce an electric signal for energizing said piezoelectric element.

4. An ultrasonic probe comprising:

a piezoelectric element emitting an ultrasonic wave and receiving an echo thereof, said piezoelectric element converting the echo into an electric signal;

a holding member holding said piezoelectric element;

a rotating mechanism rotating said holding member about the first axis;

a rotary base supporting said rotating mechanism;

a fixed chassis supporting said rotary base so as to allow said rotary base to swing about a second axis extending in a direction different from the first axis; and a swinging mechanism swinging said rotary base;

said swinging mechanism including a rotary base swinging electric motor, a motor angular position measuring encoder measuring an angular position of said rotary base swinging electric motor, and a gear train transmitting output torque of said rotary base swinging electric motor to said rotary base to swing said rotary base.

5. An ultrasonic probe comprising:

a piezoelectric element emitting an ultrasonic wave and receiving an echo thereof, said piezoelectric element converting the echo into an electric signal;

a holding member holding said piezoelectric element;

a rotating mechanism rotating said holding member about the first axis;

a rotary base supporting said rotating mechanism;

a fixed chassis supporting said rotary base so as to allow said rotary base to swing about a second axis extending in a direction different from the first axis; and a swinging mechanism swinging said rotary base;

said swinging mechanism including a voice coil motor and a rotary base angular position measuring encoder which measures an angular position of said rotary base, the voice coil motor being implemented by a magnet installed on one of said rotary base and said chassis and an electric coil installed on the other of said rotary base and said chassis.

6. An ultrasonic probe as set forth in claim 5, further comprising a holding mechanism designed to hold said rotary base on said chassis.

7. An ultrasonic probe comprising:

a piezoelectric element emitting an ultrasonic wave and receiving an echo thereof, said piezoelectric element converting the echo into an electric signal;

a holding member holding said piezoelectric element;

a rotating mechanism rotating said holding member about the first axis;

a rotary base supporting said rotating mechanism;

a fixed chassis supporting said rotary base so as to allow said rotary base to swing about a second axis extending in a direction different-from the first axis; and a swinging mechanism swinging said rotary base; and a second piezoelectric element installed on said holding member which produces an ultrasonic wave having a frequency different from that produced by said piezoelectric element.

8. An ultrasonic probe as set forth in claim 3, further comprising a magnetoresistive element responsive to a change in magnetic flux produced by the magnetic member of the second encoder to provide a signal indicative of a neutral position of said holding member in swinging motion of said holding member.

9. An ultrasonic probe as set forth in claim 3, further comprising an array of magnetoresistive elements installed on said chassis, each of the magnetoresistive element being responsive to a change in magnetic flux produced by the magnetic member of the second encoder to provide a signal indicative thereof.

* * * * *